(12) United States Patent
Hauke et al.

(10) Patent No.: US 11,679,191 B2
(45) Date of Patent: Jun. 20, 2023

(54) DEVICE FOR MONITORING THE VASCULAR ACCESS IN AN EXTRACORPOREAL BLOOD TREATMENT

(71) Applicant: FRESENIUS MEDICAL CARE DEUTSCHLAND GMBH, Bad Homburg (DE)

(72) Inventors: Christopher Hauke, Mainz-Kostheim (DE); Lars Offermanns, Butzbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 175 days.

(21) Appl. No.: 16/976,146

(22) PCT Filed: Mar. 7, 2019

(86) PCT No.: PCT/EP2019/055729
§ 371 (c)(1),
(2) Date: Aug. 27, 2020

(87) PCT Pub. No.: WO2019/175021
PCT Pub. Date: Sep. 19, 2019

(65) Prior Publication Data
US 2020/0405942 A1 Dec. 31, 2020

(30) Foreign Application Priority Data
Mar. 16, 2018 (DE) ...................... 10 2018 106 226.5

(51) Int. Cl.
*A61M 1/36* (2006.01)
*A61M 1/10* (2006.01)
*A61M 60/113* (2021.01)

(52) U.S. Cl.
CPC ........ *A61M 1/3656* (2014.02); *A61M 60/113* (2021.01); *A61M 2205/18* (2013.01);
(Continued)

(58) Field of Classification Search
CPC .............. A61M 1/3656; A61M 60/113; A61M 2205/18; A61M 2205/3306;
(Continued)

(56) References Cited

U.S. PATENT DOCUMENTS 5,792,117 A * 8/1998 Brown ...................... G01F 3/16
604/207
2003/0236445 A1* 12/2003 Couvillon, Jr. ........ A61B 5/062
600/114

(Continued)

FOREIGN PATENT DOCUMENTS

DE 102011109378 A1 2/2013
DE 102015011423 A1 3/2017
(Continued)

OTHER PUBLICATIONS

International Search Report and Written Opinion issued in corresponding International Patent Application No. PCT/EP2019/055729 (with English translation of International Search Report) dated Jun. 12, 2019 (17 pages).
(Continued)

*Primary Examiner* — Adam Marcetich
*Assistant Examiner* — Rachel O'Connell
(74) *Attorney, Agent, or Firm* — Kilyk & Bowersox, P.L.L.C.

(57) ABSTRACT

A device and method are provided for monitoring access to a patient by a device that withdraws liquid from the patient and/or supplies liquid to the patient, via a flexible line. A vessel access can be monitored during an extracorporeal blood treatment for which the blood of a patient is with-
(Continued)

drawn via a flexible arterial line having an arterial puncture cannula, and supplied to the patient via a flexible venous line having a venous puncture cannula. The monitoring device has a line guide for loosely guiding a line segment of the flexible line. By detecting a change in situation of the loosely guided line segment, a conclusion is made as to whether an incorrect vessel access has occurred.

10 Claims, 9 Drawing Sheets

(52) U.S. Cl.
CPC ............... *A61M 2205/3306* (2013.01); *A61M 2205/3317* (2013.01)

(58) Field of Classification Search
CPC ...... A61M 2205/3317; A61M 25/0008; A61M 25/01; A61M 25/02
See application file for complete search history.

(56) References Cited

U.S. PATENT DOCUMENTS

| | | | | |
|---|---|---|---|---|
| 2005/0011282 | A1* | 1/2005 | Voege | A61M 16/0841 73/861.44 |
| 2008/0283343 | A1* | 11/2008 | Kunz | B66B 1/3492 187/394 |
| 2009/0306574 | A1* | 12/2009 | Kopperschmidt | A61M 1/3655 604/6.16 |
| 2013/0035627 | A1 | 2/2013 | Bongers | |
| 2014/0183106 | A1* | 7/2014 | Kotsos | B01D 61/30 210/85 |
| 2016/0061641 | A1* | 3/2016 | Peret | G06K 9/6215 73/861.41 |
| 2016/0144096 | A1* | 5/2016 | Stefani | A61B 5/6866 604/6.09 |
| 2016/0239635 | A1* | 8/2016 | Fateh | A61M 15/008 |
| 2016/0311649 | A1* | 10/2016 | Puranen | B66B 1/3492 |
| 2016/0367751 | A1* | 12/2016 | Bazargan | F04B 51/00 |
| 2018/0016117 | A1* | 1/2018 | Palazzola | B66B 7/1238 |
| 2020/0016316 | A1 | 1/2020 | Heide et al. | |

FOREIGN PATENT DOCUMENTS

| | | |
|---|---|---|
| DE | 102017106403 A1 | 9/2018 |
| WO | 2007104350 A1 | 9/2007 |
| WO | 2009042259 A1 | 4/2009 |
| WO | 2013117252 A1 | 8/2013 |
| WO | 2016023868 A1 | 2/2016 |

OTHER PUBLICATIONS

Wikipedia—Linear ball bearings (2017) (with English translation).
International Preliminary Report on Patentability issued in corresponding International Patent Application No. PCT/EP2019/055729 (English translation) dated Sep. 22, 2020 (8 pages).

* cited by examiner

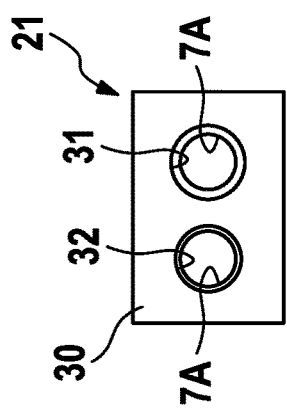
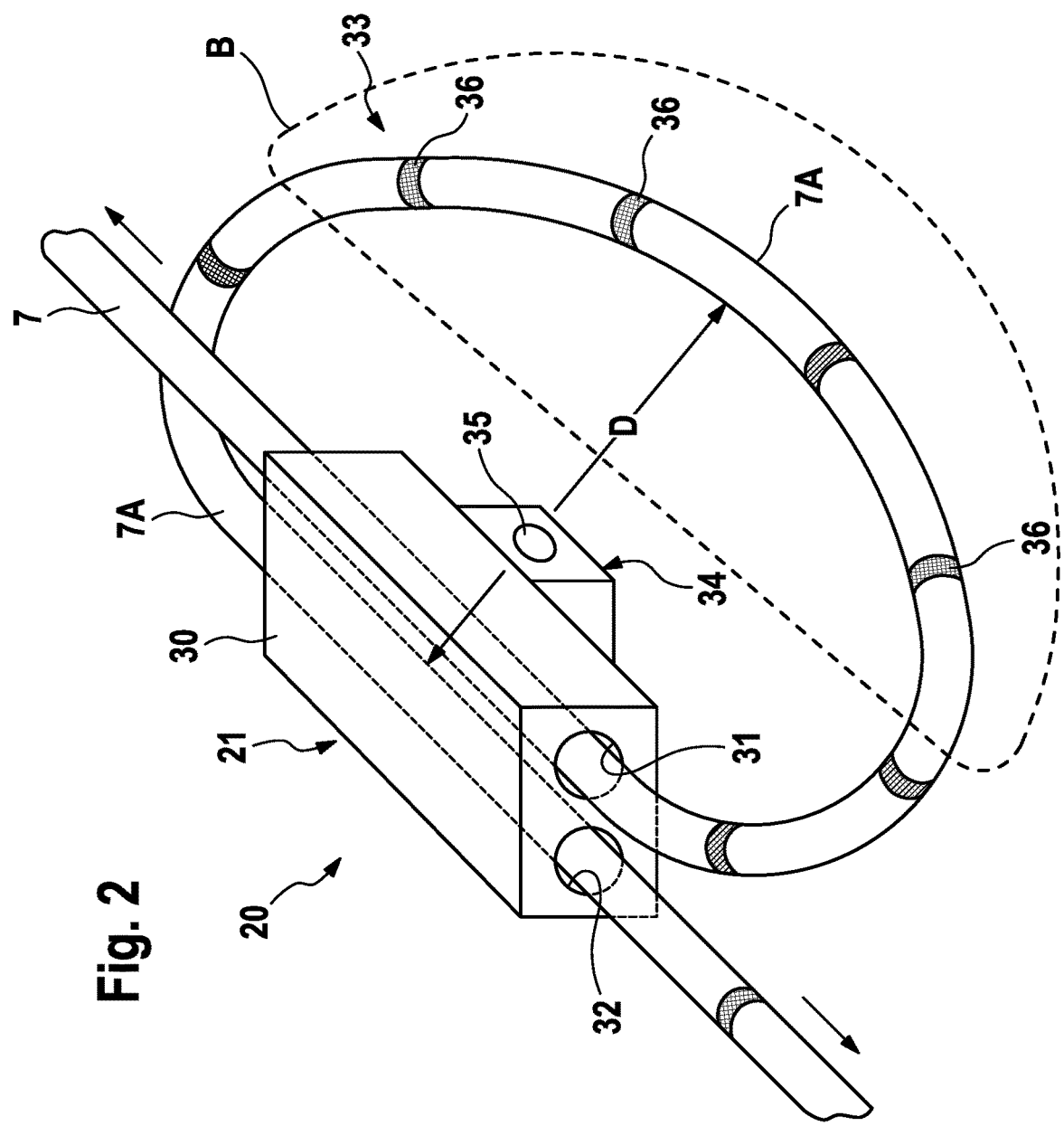

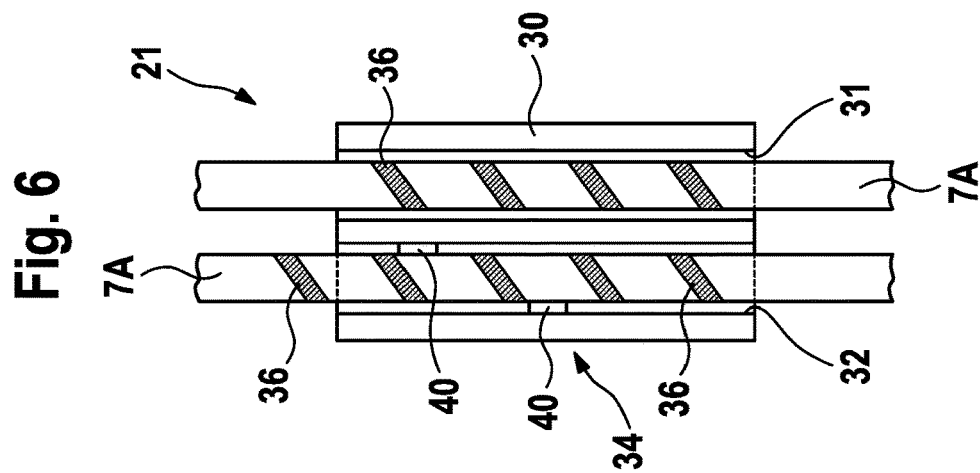
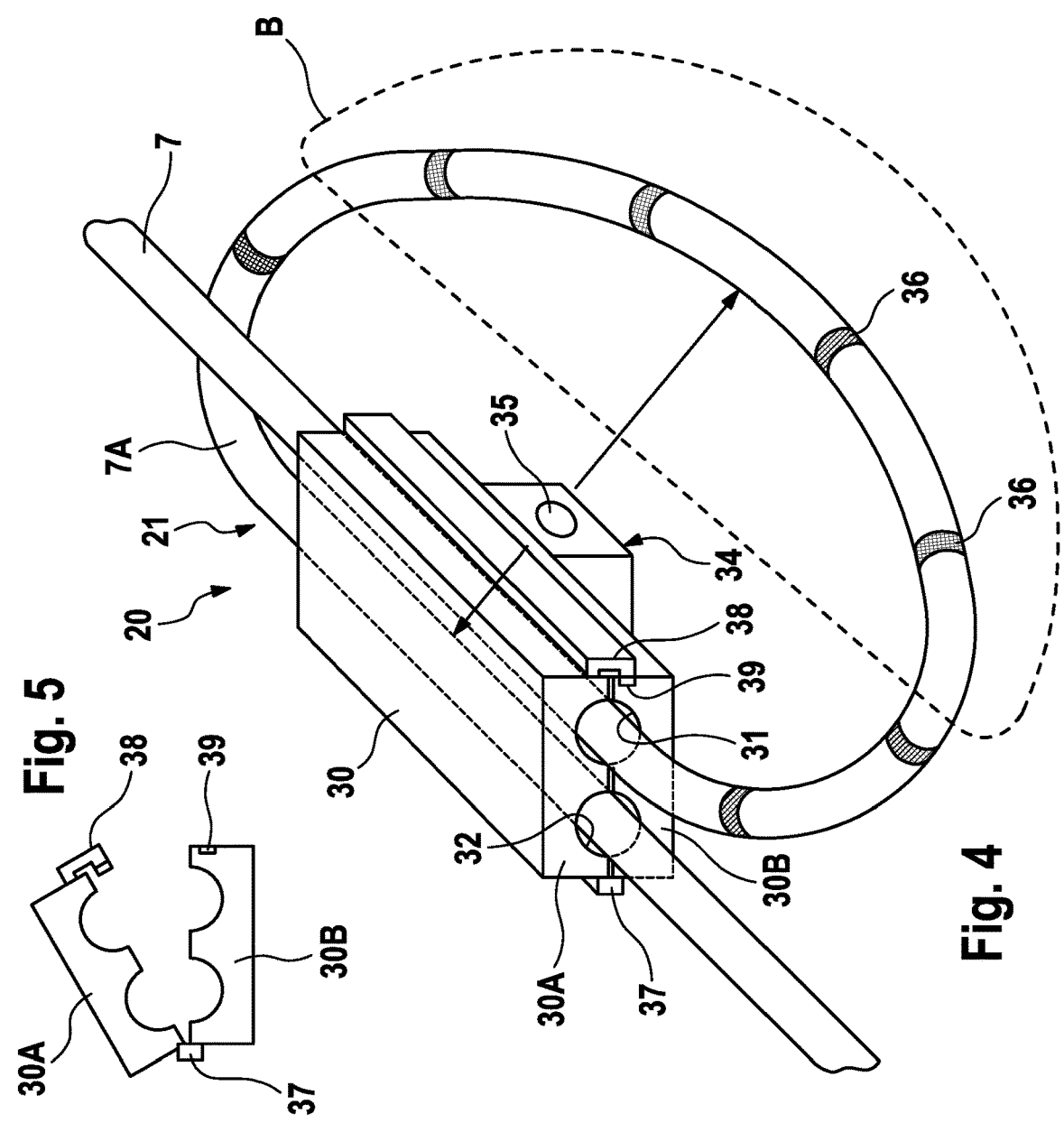

DEVICE FOR MONITORING THE VASCULAR ACCESS IN AN EXTRACORPOREAL BLOOD TREATMENT

CROSS-REFERENCE TO RELATED APPLICATIONS

This application is a National Stage Application of PCT/EP2019/055729, filed Mar. 7, 2019, which claims priority to German Patent Application No. 10 2018 106 226.5, filed Mar. 16, 2018.

BACKGROUND OF THE INVENTION

The invention relates to a device for monitoring access to a patient for a device by means of which a liquid is withdrawn from the patient and/or supplied to the patient via a flexible line, in particular for monitoring vessel access during extracorporeal blood treatment, in which blood of a patient is withdrawn from the patient via a flexible arterial line having an arterial puncture cannula and supplied to the patient via a flexible venous line having a venous puncture cannula. The invention further relates to a blood treatment device comprising a device for monitoring access to a patient and to a method for monitoring access to a patient for withdrawing and/or supplying a liquid from and/or to the patient.

In the field of medical technology, a number of apparatuses are known by means of which liquids can be supplied to a patient or withdrawn from the patient via a flexible line. In this context, access to the patient is generally achieved by means of a catheter for introduction into bodily organs or a cannula or needle for puncturing vessels. During analysis or treatment, proper access to the patient has to be ensured. It is therefore necessary to monitor patient access.

One application scenario involving particularly high safety requirements for vessel access is extracorporeal blood treatment, in which blood is withdrawn from the patient via a flexible arterial line having an arterial puncture cannula, passed through a dialyser, and supplied to the patient again via a flexible venous line having a venous puncture cannula. In this context, in spite of routine monitoring of patient access by hospital staff, there is always the risk that the venous puncture cannula may slip out of the patient's blood vessel unnoticed. Whilst the arterial cannula slipping out can lead to suction of air into the flexible arterial line, which results in an alarm and interruption of the treatment because air is detected by the machine, the venous cannula slipping out and the resulting risk of blood flowing freely into the environment cannot readily be detected. However, if it is not immediately detected that the venous cannula has slipped out, the patient can bleed out.

The safety devices which are present as standard in treatment machines are generally based on monitoring the pressure in the extracorporeal blood circuit. In practice, however, it has been found that in particular the venous puncture cannula slipping out cannot be detected sufficiently reliably merely by monitoring the pressure in the extracorporeal blood circuit.

WO 2007/104350 A1 and WO 2013/0117252 disclose devices which are simple to handle, can be manufactured cost-effectively, can be retrofitted at any time, and which make reliable monitoring of patient access possible. The monitoring of the patient access is based on a loop being formed in the liquid-conveying flexible line. It is assumed that if the puncture cannula slips out this is due to the action of tensile forces on the flexible line. When tension is applied to the flexible line, the loop necessarily tightens. This leads to an increased pressure loss in the flexible line, which is detected by a pressure sensor. For fixing the flexible line in the shape of a loop, WO 2007/104350 A1 and WO 2013/0117252 propose the use of fixing elements for fixing the flexible line in the shape of a loop and by means of which a line segment of the flexible line is fixed in the shape of a loop, in such a way that the loop can tighten when tension is applied. In WO 2007/104350 A1, however, it is found to be disadvantageous that the tensile forces required for this purpose are relatively high. Therefore, if there are merely low tensile forces, it cannot be ensured that incorrect vessel access is detected. To reduce the tensile forces, WO 2013/0117252 proposes a fixing element comprising a guide piece and a securing piece.

SUMMARY OF THE INVENTION

An object of the invention is to create a device for monitoring access to a patient which is simple to handle, can be manufactured cost-effectively and can be retrofitted at any time, and which makes it possible to detect incorrect vessel access reliably even if there is only a low tension applied to the flexible line, and to provide a blood treatment device comprising a device of this type for monitoring access to a patient.

The object of the invention relates both to access to vessels such as a fistula or shunt in chronic extracorporeal blood treatment, which are punctured using needles or cannulas, and to catheters, for example central venous catheters in acute extracorporeal blood treatment, for example extracorporeal critical care therapy (ECCT), in particular continuous renal replacement therapy (CRRT), as well as infusion technology.

A further object of the invention is to set out a cost-effective method which is simple to handle, by means of which incorrect vessel access can be detected reliably even if only a low tension is applied to the flexible line.

These objects are achieved in accordance with the invention by the features of the independent claims. Advantageous embodiments of the invention form the subject matter of the dependent claims.

The object is achieved both for access to vessels such as a fistula or shunt in chronic extracorporeal blood treatment, which are punctured using needles or cannulas, and for central venous catheters in acute extracorporeal blood treatment, for example extracorporeal critical care therapy (ECCT), in particular continuous renal replacement therapy (CRRT), as well as infusion technology. Whenever reference is made to needles, puncture cannulas or cannulas, this applies equally to catheters, for example central venous catheters in acute extracorporeal blood treatment.

Incorrect vessel access means not only the puncture cannula slipping out completely, but also incorrect positioning of the cannula, for example if the puncture cannula has only slipped out in part.

The device according to the invention and the method according to the invention for monitoring patient access are based on a line segment of the flexible line being guided loosely. A line guide is used for this purpose, and may be part of the flexible line or be loosely attached to the flexible line.

For the invention, it is irrelevant whether the loosely guided line segment is distinguished by the shape of a circle, in which the ends of the line segment cross, for example the line segment forming a loop or noose, or distinguished merely by the shape of a curved portion, the ends of which do not cross. The device according to the invention and the method according to the invention are not based on monitoring a change in pressure in the flexible line caused by an increase in the pressure loss due to a reduction in the diameter of the loop, but rather on detecting a change in situation in the line segment due to an applied tension, it being concluded that incorrect vessel access is occurring if the situation of the line segment changes. Since only changes in situation are monitored, even slight applied tensions are already sufficient to indicate incorrect vessel access. In the device according to the invention and the method according to the invention, the change in situation does not have to lead to an increase in the pressure loss in the line segment to indicate incorrect vessel access.

The invention provides various apparatuses for detecting the situation of the line segment, which differ in that the situation detection may be contactless or non-contactless. However, it is common to all of the apparatuses for situation detection that they are part of the line guide. The device according to the invention thus forms a unit which is simple to handle and which can be attached to the flexible line or may already be connected to the flexible line.

In the present invention, detecting the situation of a line segment may mean detecting each change in situation of the line segment or each change in position of the line segment relative to the line guide and/or relative to the apparatus for situation detection. A change in situation means for example a change in the diameter of the loop or in the length or width of the arc-shaped portion. In some embodiments, the change in situation in the line segment or in a portion thereof may take place in an axial direction of the central longitudinal axis of the line segment. In other embodiments, the change in situation of the line segment or of a portion thereof may deviate from the axial direction of the central longitudinal axis of the line segment.

After the fistula or shunt is punctured by means of the cannula or needle, or after a central venous catheter is placed, the flexible line is laid so as to be free from tensile forces, and the line segment is guided through the line guide according to the invention without any tensile forces, in such a way that a change in situation of the line segment is possible within a particular range without the threat of an inadmissible tensile force on the cannula or needle or the central venous catheter. In the present invention, an inadmissible change in situation of the line segment means any change in situation of the line segment or any change in position of the line segment relative to the line guide and/or relative to the apparatus for situation detection for which there is the risk of an inadmissible tensile force on the cannula or needle or the central venous catheter such that there is a threat of the cannula or needle or the central venous catheter being pulled out of the patient's blood vessel system. Therefore, in practice, only slight changes in situation should be possible.

In some embodiments, the apparatus for situation detection comprises an optical image capture system. In the present invention, an optical image capture system means a detection system configured to detect a change in the spatial situation of a flexible line using light. Examples include phototransistors, for example for colour detection and/or brightness/darkness detection and/or opacity detection, and sensors for capturing two-dimensional photographs such as CCD sensors and CMOS sensors.

In some embodiments, the optical image capture system is configured to detect a plurality of spaced-apart markings, applied to the flexible line (7), individually in succession, and to count when the markings are moved relative to the optical image capture system, as a result of a change in situation of the flexible line, and pass through the detection region thereof, the optical image capture system having an evaluation unit, which is configured in such a way that the number of counted markings is compared with a predetermined threshold and it is concluded that there is a change in situation of the flexible line due to tension applied to the flexible line if the number of counted markings is greater than a predetermined threshold.

The markings need not be provided over the entire length of the flexible line, but merely on the line segment which is loosely guided by means of the line guide. The markings may be stripes on the flexible line which are provided on the flexible line at a predetermined interval. The markings may for example be glued or printed onto the flexible line or applied thereto in the form of a coating.

An alternative embodiment provides for the optical image capture system to be configured in such a way that a plurality of markings provided on the flexible line is determined within an observation window, the optical image capture system having an evaluation unit, which is configured in such a way that the number of markings in the observation window is compared with a predetermined threshold and it is concluded that there is a change in situation of the flexible line due to tension applied to the flexible line if the number of counted markings is less than a predetermined threshold or the number decreases by a predetermined number. The observation window may be any image portion which can easily be captured by the image capture system. Preferably, the portion of the line segment which changes in situation particularly greatly when tension is applied should be positioned in the observation window, for example a portion, not covered by the line guide, of the line segment which forms a loop.

The optical image capture system may also be configured in such a way that the distance between any markings provided on the flexible line and positioned in the observation window is determined, the optical image capture system having an evaluation unit, which is configured in such a way that the distance between the markings in the observation window is compared with a predetermined threshold and it is concluded that there is a change in situation of the flexible line due to tension applied to the flexible line if the distance between the markings is less than a predetermined threshold.

A further embodiment provides for the apparatus for situation detection to have a tactile sensor system, which is configured in such a way that a change in situation of the flexible line due to tension applied to the flexible line is detected. The tactile sensor system may have a tactile sensor which can be brought, under resilient bias, against the line segment guided by means of the line guide.

One embodiment of a tactile sensor system comprising a tactile sensor has an evaluation unit, which receives the measurement signal of a displacement meter, which is designed in such a way that the distance by which the tactile sensor is displaced when the situation of the line segment changes is measured. The evaluation unit may be configured in such a way that the measured displacement is compared with a predetermined threshold and it is concluded that there is a change in situation of the flexible line due to tension applied to the flexible line if the measured displacement is greater than a predetermined threshold or changes by a predetermined amount. The displacement meter may be any measurement value sensor which generates a signal proportional to the displacement.

An alternative embodiment provides for the tactile sensor to be designed as an actuation member of an electrical switch. In this embodiment, the tension applied to the flexible line leads to deflection of the tactile sensor, causing the switch for example to be closed in such a way that a current flows in a circuit. This embodiment is distinguished by particularly simple and cost-effective manufacture.

The apparatus for situation detection may also have an elongate actuation element, which actuates an electrical switch when deformed. In this embodiment, the first end of the elongate actuation element is in operative connection with a first portion of the line segment guided by means of the line guide, whilst the second end of the elongate actuation element is in operative connection with a second portion of the line segment guided by means of the line guide. Since the two ends of the elongate actuation element are in operative connection with different portions of the line segment, in the event of a change in situation of the line segment due to applied tension, the actuation element is deformed in such a way that the electrical switch is actuated. The actuation element may for example be a strip-shaped or rod-shaped, preferably resilient element made of metal or plastics material.

The apparatus for situation detection may also have an elongate element made of an electrically conductive material, the first end of the electrically conductive element being in operative connection with a first portion of the line segment guided by means of the line guide, and the second end of the electrically conductive element being in operative connection with a second portion of the line segment guided by means of the line guide, in such a way that the elongate element is severed in the event of a change in situation of the line segment due to applied tension. The elongate element may be a single electrical wire to which tension is applied in the event of a change in situation of the line segment. The apparatus for situation detection may have an evaluation unit, which is configured in such a way that the electrical resistance of the electrically conductive element is monitored. In an embodiment which is particularly simple to manufacture and cost-effective, the wire may be part of a circuit which is interrupted in the event of a change in situation.

Furthermore, the apparatus for situation detection may have a roller, which comprises a rotation meter and can be brought into contact with the line segment guided in the line guide, an evaluation unit which receives the measurement signal of the rotation meter being provided and being configured in such a way that the number of rotations of the roller is compared with a predetermined threshold. The roller comprising the rotation meter makes it possible to detect an axial displacement of a portion of the line segment due to applied tension. At the same time, the roller may provide better guidance of the line segment in the line guide, in such a way that even low tensile forces can lead to changes in situation. For loose guidance of the line segment in the line guide, a plurality of rollers may also be provided. However, in this case, it is only necessary to provide a rotation meter on one of the rollers.

One embodiment provides a line guide which is designed in such a way that the line segment is guided in the shape of a loop, which contracts if tension is applied. This line guide may have a housing body, comprising a first guide channel for receiving a first portion of the line segment and a second guide channel for receiving a second portion of the line segment of the flexible line, in such a way that the line segment can be fixed in the shape of a loop. The diameter of at least one of the two guide channels is dimensioned in such a way that a portion of the line segment is guided loosely, in such a way that the loop can contract if tension is applied. So as to be able to lay the line segment in the line guide in a simple manner, the housing body may have two housing halves, it being possible for the guide channels to be formed in the first and/or second housing half of the housing body. The first and/or second housing half of the housing body may for example be releasably or openably interconnected. The releasable connection may for example be a latch connection or snap-on connection. The two housing halves may also be connected using brackets or the like. The openable connection may be a connection comprising hinges, such that the housing body can be folded open. The housing body may be an injection-moulded part, it being possible for the hinges to be film hinges. However, the housing body may also consist of only one piece.

In an alternative embodiment, the flexible line is formed in such a way that the line segment is guided in the shape of an arc, in other words guided in such a way that the line segment does not form a circle. In this embodiment, the line guide may have a housing body, in which an arc-shaped contact face for the line segment is formed, such that the line segment is fixed in the shape of an arc. Application of tension to the flexible line leads to deformation of the arc, and this results in a change in situation of the line segment.

A further embodiment provides for the line guide to have an arc-shaped guide element for receiving the line segment. In this embodiment, the arc-shaped guide element may have a first arc-shaped portion for receiving a first sub-portion of the line segment and a second arc-shaped portion for receiving a second sub-portion of the line segment, the first and second portions of the guide element being movably interconnected in such a way that the distance between the opposite ends of the arc-shaped portions of the guide element increases when tension is applied to the flexible line. The arc-shaped guide element for receiving the line segment may be a profiled piece which is designed in such a way that the line segment can be laid so as to fit into the profiled piece. The arc-shaped guide element may also consist of a resilient material, such that the distance between the opposite ends of the arc-shaped portions of the guide element increases when tension is applied to the flexible line. In this embodiment, a movable connection between two sub-portions is not required, and so the line guide can be manufactured in a particularly simple and cost-effective manner.

The apparatus for situation detection may be configured in such a way that a control signal is generated when a change in situation of the line segment due to tension applied to the flexible line is detected and it is concluded that incorrect vessel access is occurring. In this connection, a control signal means any signal which can be subjected to further signal processing.

The device according to the invention for monitoring access to a patient may in particular be used in a blood treatment device comprising an extracorporeal blood circuit which has a flexible arterial line comprising an arterial puncture cannula and a flexible venous line comprising a venous puncture cannula. The blood treatment device may have an alarm unit, which is configured in such a way that an alarm is provided if the apparatus for situation detection detects a change in the situation of the line segment due to tension applied to the flexible line. In the blood treatment device, which has a blood pump for conveying blood in the extracorporeal blood circuit and a venous blocking member for blocking the flexible venous line, a control unit may be provided, which is configured in such a way that the blood pump is stopped and/or the venous blocking member is closed if the apparatus for situation detection detects a change in situation of the line segment.

For wirelessly transmitting a control signal, the apparatus for monitoring vessel access may have a transmitter and the blood treatment device may have a receiver. The signal may be transmitted using optical signals and/or electrical signals (radio). However, it is also possible for the apparatus for monitoring the vessel access and the blood treatment device to be interconnected using an electrical connection cable.

BRIEF DESCRIPTION OF THE DRAWINGS

Hereinafter, various embodiments of the invention are described in greater detail with reference to the drawings, in which:

FIG. 2 shows a first embodiment of the device according to the invention for monitoring patient access, in which the change in situation of the flexible line is detected optically, FIG. 3 is a partial view of an alternative embodiment of the first embodiment of the device according to the invention, FIG. 4 shows a further embodiment of the device according to the invention for monitoring patient access, in which the change in situation of the flexible line is detected optically, FIG. 5 is a front view of the embodiment from FIG. 4, with the line guide open, FIG. 6 shows a further embodiment of the device according to the invention for monitoring patient access, in which the change in situation of the flexible line is detected optically.

DETAILED DESCRIPTION OF THE INVENTION

Figure 1:
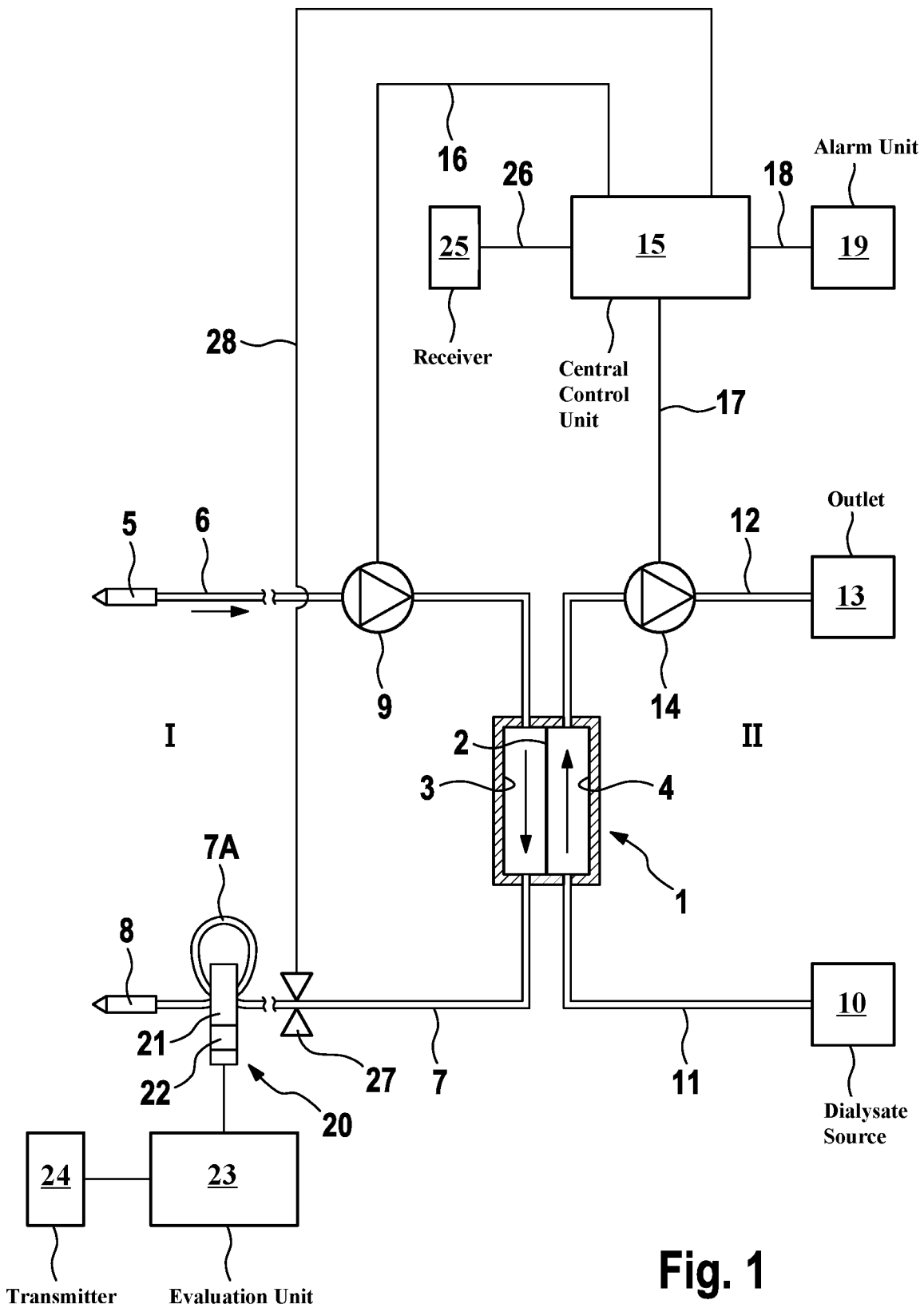
FIG. 1 is a highly simplified schematic drawing of the essential components of a blood treatment device together with the device according to the invention for monitoring patient access.

FIG. 1 shows the essential components of a blood treatment device, by way of example a haemodialysis device, which has a device for monitoring venous vessel access. The blood treatment device has a dialyser 1, which is subdivided by a semipermeable membrane 2 into a blood chamber 3 and a dialysate chamber 4. A flexible arterial line 6 is connected to the fistula or shunt of the patient by means of an arterial puncture cannula 5, and leads to the inlet of the blood chamber 3 of the dialyser 1. A flexible venous line 7 leads away from the outlet of the blood chamber 3 of the dialyser 1, and is connected to the fistula or shunt of the patient by means of a venous puncture cannula 8. The flexible arterial line 6 is laid in an occlusive blood pump 9, which conveys the blood in the extracorporeal blood circuit I.

The dialysate circuit II of the blood treatment device comprises a dialysate source 10, to which a dialysate supply line 11 is connected, which leads to the inlet of the dialysate chamber 4 of the dialyser. A dialysate withdrawal line 12 leads away from the outlet of the dialysate chamber 4 of the dialyser 1 and leads to an outlet 13. A dialysate pump 14 is connected into the dialysate withdrawal line 12.

The blood treatment device is controlled by a central control unit 15, which actuates the blood and dialysate pump 9, 14 via control lines 16, 17. The central control unit 15 is connected via a data line 18 to an alarm unit 19, which provides an optical and/or acoustic and/or tactile alarm in the event of an abnormal occurrence.

The blood treatment device has a device 20 for monitoring venous vessel access. The monitoring device 20 comprises a line guide 21 (merely shown schematically in FIG. 1) which loosely fixes a line segment 7A of the flexible venous line 7 in a particular shape, for example in the shape of a loop. The monitoring device 20 further has an apparatus 22 (merely shown schematically in FIG. 1), for detecting the situation of the line segment 7A guided by means of the line guide 21, and an evaluation unit 23. The evaluation unit 23 generates a control signal if a change in situation of the line segment 7A is detected. The monitoring device 20 further has a transmitter 24 which emits the control signal. The blood treatment device has a receiver 25 which receives the control signal. The receiver 25 is connected to the central control unit 15 of the blood treatment device via a data line 26.

A blocking member 27, for example an electromagnetically actuable venous line clamp, is located downstream from the blood chamber 3 of the dialyser on the flexible venous line 7, and is closed by the central control unit 15 via a further control line 28 if the receiver 25 receives the control signal from the monitoring device 20 signalling an inadmissible change in situation of the line segment 7A. In this case, the control unit 15 stops the blood pump 9 and/or closes the blocking member 27, in particular the venous line clamp.

Hereinafter, various embodiments of the monitoring device 20 are disclosed in detail.

FIG. 2 is a perspective drawing of a first embodiment of the monitoring device 20, which has an optical image capture system. The line guide 21 has a housing body 30, which is manufactured by injection moulding and which has two guide channels 31, 32, which extend mutually parallel and the internal diameter of which is greater than the external diameter of the flexible line 7. The two end portions of a line segment 7A, which forms a loop 33, of the flexible line 7 are guided loosely in the two guide channels 31, 32. If a tensile force is exerted on the ends of the flexible line, as indicated by arrows in FIG. 2, the loop 33 contracts. The housing body 30 of the line guide 21 may be shaped differently, for example in the shape of a cuboid or in an arc shape.

FIG. 3 is a front view of the line guide 21 of an alternative embodiment, which differs from the embodiment from FIG. 2 in that only a portion of the line segment 7A is guided loosely in a guide channel 31, in such a way that the loop 33 only contracts if the loosely guided line portion is pulled on.

If the loop 33 contracts when tension is applied, the situation of the line segment 7A guided in the line guide 21 changes, the diameter D of the line segment decreasing. The apparatus 22 for detecting the situation of the line segment has an optical image capture system 34, which has an evaluation unit 23 (FIG. 1) which evaluates the image data. The optical image capture system 34 located in the housing body 30 has an optical sensor 35, for example a CCD sensor, which captures an image region in which the loop 33 is positioned. To detect a change in situation of the line segment 7A, the image processing methods known to a person skilled in the art may be used.

To simplify the situation detection using the optical image capture system, the flexible line may be provided with markings 36, for example in the form of stripes. The stripes, which are of a predetermined width and arranged at a predetermined distance from one another, can easily be detected by the image capture system 34. When the loop 33 contracts, in other words when there is a change in situation in the line segment 7A, the distance between the individual markings decreases. Furthermore, the number of markings 36 decreases for a predetermined observation window B, which is determined by the image region of a sub-region of the image region captured by the optical sensor 35.

The evaluation unit 23 is configured in such a way that the distance between any two markings of a plurality of markings 36 is determined and compared with a predetermined threshold, and it is concluded that there is a change in situation of the flexible line if the distance between the markings 36 is less than a predetermined threshold or decreases by a particular amount. Alternatively or in addition, the evaluation unit 23 may be configured in such a way that the number of markings 36 in the observation window B is determined and compared with a predetermined threshold, and it is concluded that there is a change in situation of the flexible line if the number of markings 36 is less than a predetermined threshold or decreases by a particular number.

Instead of an optical image capture system 34, a distance sensor, for example an optical distance sensor or an ultrasound distance sensor, which measures the distance from the opposite portion of the loop segment 7A, may be integrated into the housing body of the line guide. The evaluation unit 23 is configured in such a way that the measured distance value is compared with a predetermined threshold. If the distance value is less than the threshold or decreases by a particular amount, the control signal is generated.

FIGS. 4 and 5 show an embodiment of the monitoring device 20 which differs from the embodiment from FIG. 2 in that the housing body 30 of the line guide 21 has a first housing half 30A and a second housing half 30B, which are interconnected at a longitudinal face by a hinge 37 in such a way that the housing body 30 can be folded open. The mutually corresponding parts are provided with like reference numerals. FIG. 4 is a perspective view of the folded-up housing body 30, whilst FIG. 5 is a front view of the folded-open housing body 30. This embodiment has the advantage that the line segment 7A can be laid in the line guide 21 easily. To close the housing body 30, a bracket 38 is provided on a longitudinal face of the upper housing half 30A, and engages in a groove 39 on the lower housing half 30B by means of clamping.

FIG. 6 shows a further embodiment of the monitoring device 20, which differs from the embodiment from FIG. 2 in terms of the image capture system 34. The image capture system 34 of the embodiment from FIG. 6 does not have an optical sensor (FIG. 2) located outside the housing body 30, but rather one or more optical sensors 40 which are provided inside the housing body 30 on one or both guide channels 31, 32 of the line guide 21. The optical sensors 40 capture the markings 36 on the line segment 7A, for example in the form of stripes, which have a predetermined width and are arranged at a predetermined distance from one another. A single optical sensor 40 is sufficient for capturing the markings. The optical sensor may for example be a phototransistor which for example detects the markings using brightness/darkness detection. When the loop 33 contracts, the relevant portion of the line segment is displaced in the guide channel 32 in the longitudinal direction. The evaluation unit 23 of the image capture system 34 may be configured in such a way that the change in situation of the markings 36 is detected and if tension is applied the control signal is generated. The evaluation unit 23 may also be configured in such a way that the number of markings 36 is counted if the markings 36 are moved relative to the optical sensor 40 of the image capture system as a result of a change in situation of the flexible line (7) and pass through the capture region thereof, and the number of markings 36 is compared with a predetermined threshold. If the number of markings 36 is greater than the threshold, the control signal is generated. Since the width and spacing of the stripe-like markings 36 are known, the evaluation unit 23 can calculate the distance by which the loop 33 contracts. The markings may also consist of materials which cannot be captured optically, for example markings which cause a change in the magnetic field, inductance or capacitance. In this case, instead of optical sensors, the apparatus for situation detection has sensors for detecting these physical variables.

Figure 7:
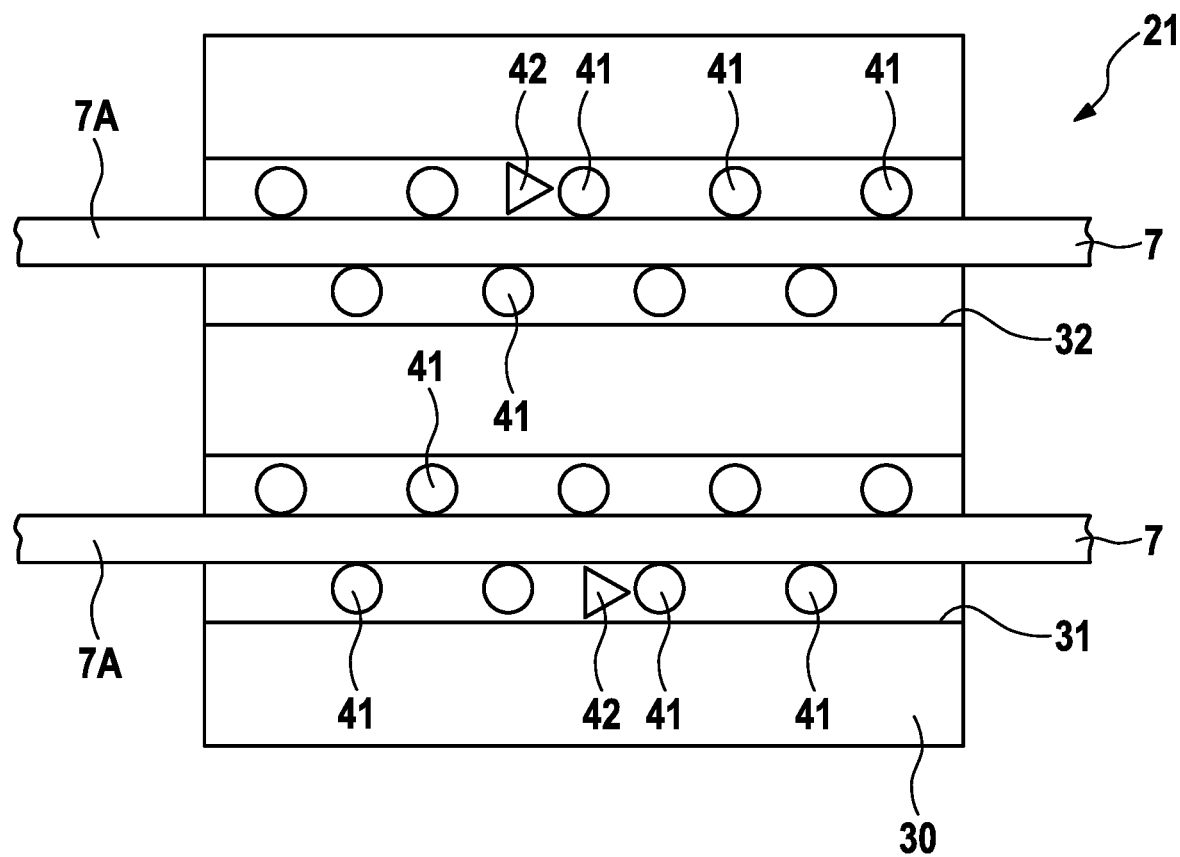
FIG. 7 shows a further embodiment of the device according to the invention for monitoring patient access, in which the change in situation of the flexible line is detected by measuring the rotations of at least one roller.

FIG. 7 shows an alternative embodiment, in which rollers 41 are provided in the housing body 30 of the line guide 21, which may be designed in accordance with FIG. 2 or FIG. 4, along at least one of the guide channels 31, 32, and can roll along on the relevant portion of the line segment 7A when it changes in situation, in such a way that the loop 33 can contract particularly easily. In this embodiment, the apparatus 22 for situation detection has a rotation meter 42 (merely shown schematically in FIG. 7), which is associated with one of the rollers 41, such that the number of rotations of the roller can be detected. Furthermore, an evaluation unit 23 which receives the measurement signal of the rotation meter 42 is provided, and is configured in such a way that the number of rotations of the roller 41 is compared with a predetermined threshold. The control signal is generated if the number of rotations is greater than the threshold.

Hereinafter, referring to FIGS. 8 to 12, further embodiments are disclosed, in which the change in situation is not detected by optical means. In the embodiments of FIGS. 8 to 12, the line segment 7A is fixed in the shape of an arc 43. However, it is also possible to apply the principle for detecting a change in situation to the other embodiments, in which the line segment 7A forms a loop 33.

Figure 8:
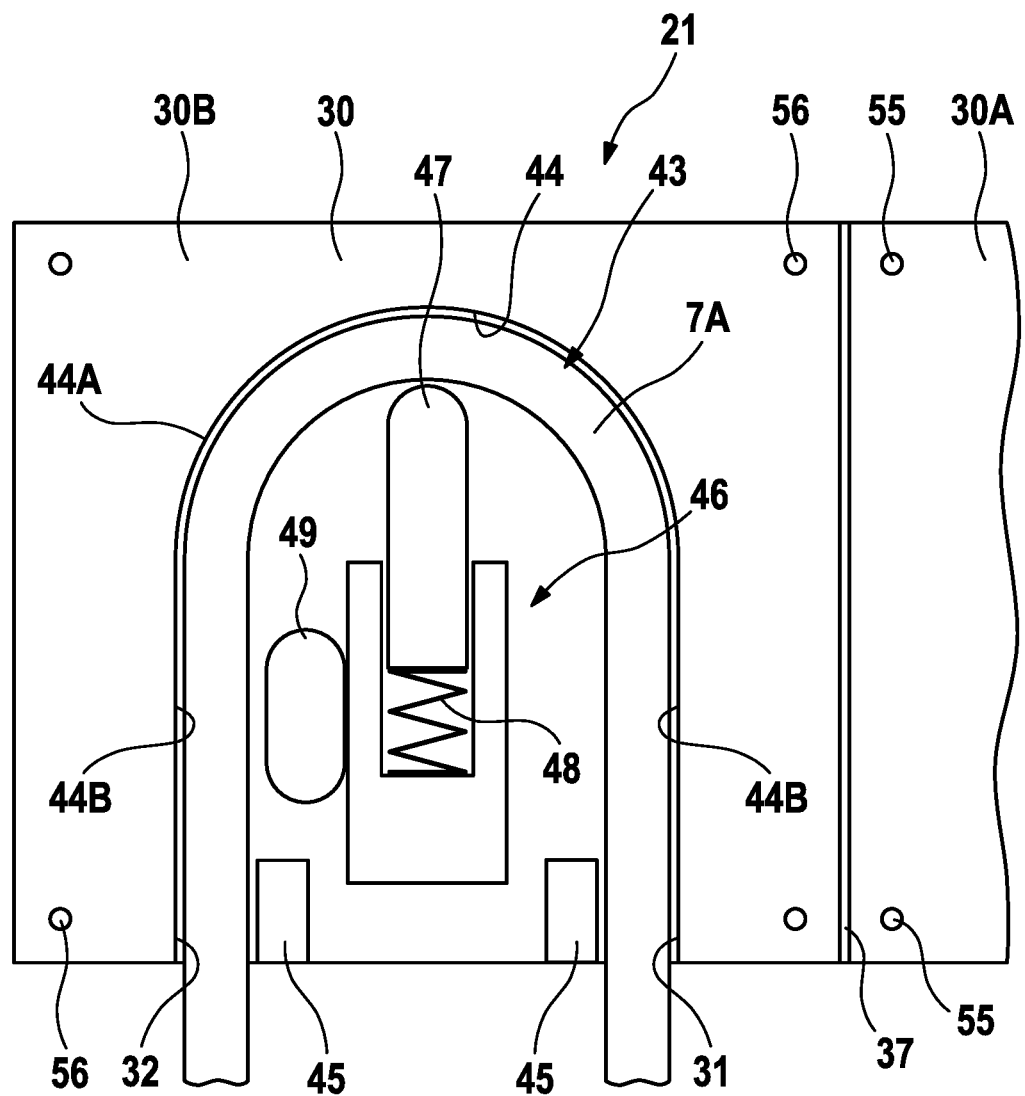
FIG. 8 shows a further embodiment of the device according to the invention for monitoring patient access, in which the change in situation of the flexible line is detected in a tactile manner.

The line guide 21 from FIG. 8 has a housing body 30 comprising a first and a second housing half, which are interconnected by a hinge 37 in such a way that the housing halves 30A, 30B can be folded together. Latch tabs 55 may be provided on one housing half 30A, which engage in recesses 56 on the other housing half 30B. One housing half 30B has an arc-shaped contact face 44 comprising a semi-circular portion 44A and two parallel straight-line portions 44B, against which the line segment 7A can be laid in such a way that the line segment is loosely fixed in the shape of an arc 43. For further guidance of the line segment 7A, further guide elements 45 may be provided, which may in particular be arranged in the regions at which the flexible line portions extend out of the housing body 30.

The apparatus 22 for situation detection has a tactile sensor system 46, which has an axially displaceably guided tactile sensor 47 which is biased against the semi-circular portion 44A of the line segment 7A by a spring 48 in such a way that the line segment is pressed against the semi-circular portion. The apparatus 22 for situation detection further comprises a displacement meter 49 (merely shown schematically in FIG. 8) and an evaluation unit 23 which receives the measurement signal of the displacement meter 49. The evaluation unit 23 is designed in such a way that the distance by which the tactile sensor 47 is displaced during a change in situation of the line segment due to tension applied to the flexible line is measured. The evaluation unit 23 compares the measured displacement with a predetermined threshold and generates the control signal if the measured distance is greater than a predetermined threshold.

Figure 9:
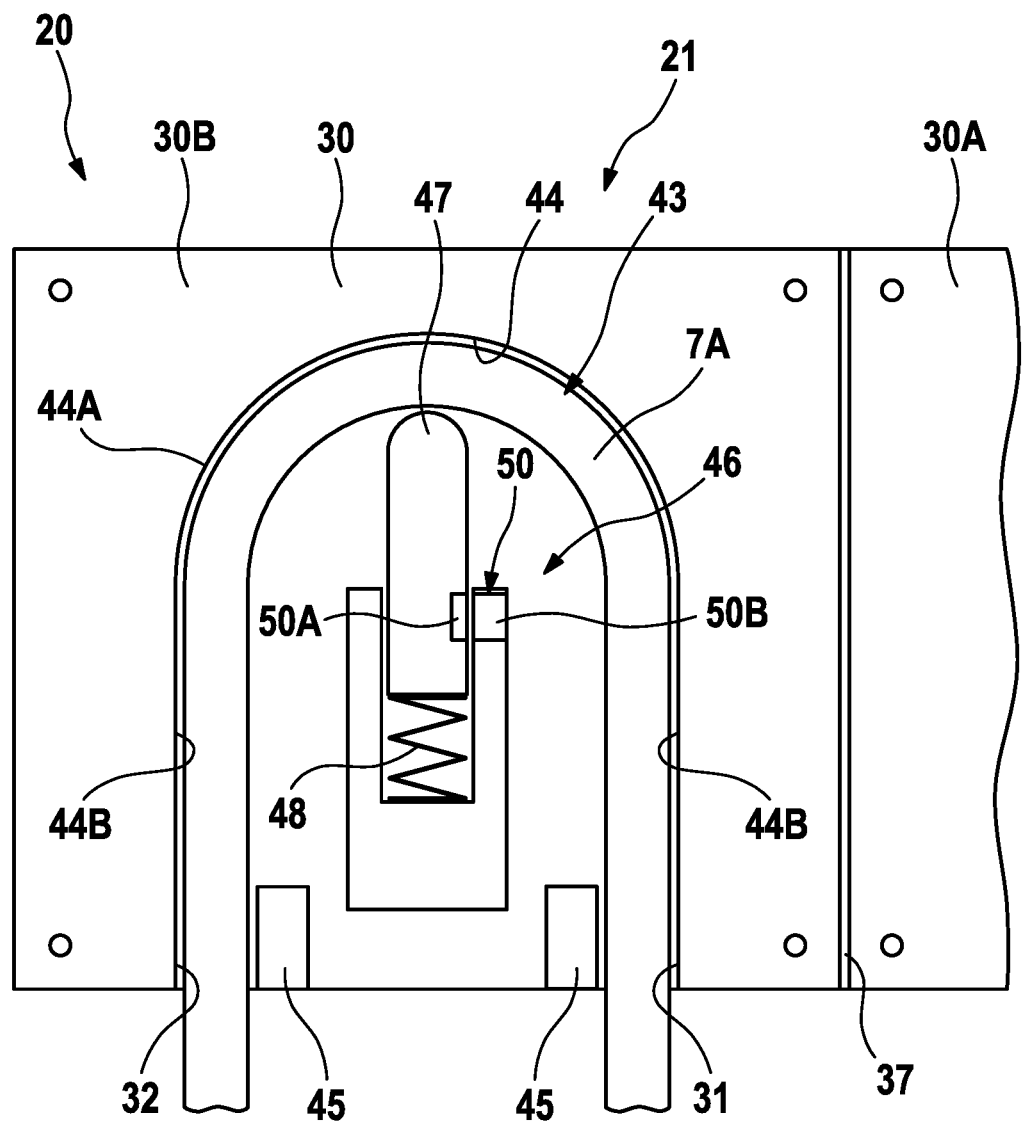
FIG. 9 shows an alternative embodiment of the device according to the invention from FIG. 8.

FIG. 9 shows an alternative embodiment which differs from the embodiment of FIG. 8 in that the tactile sensor 47 is designed as an actuation member of an electrical switch 50. The switch 50 has a first, movable switch contact 50A, which is provided on the tactile sensor 47, and a second, stationary switch contact 50B, which is provided on the housing body 30. During displacement of the tactile sensor 47 due to applied tension, the switch 50 opens. In this embodiment, for example an alarm unit 19 (FIG. 1), which may also be provided on the monitoring device 21 itself, can be switched on by the switch 50 if there is an inadmissible change in situation of the line segment 7A, without further signal processing being required.

Figure 10:
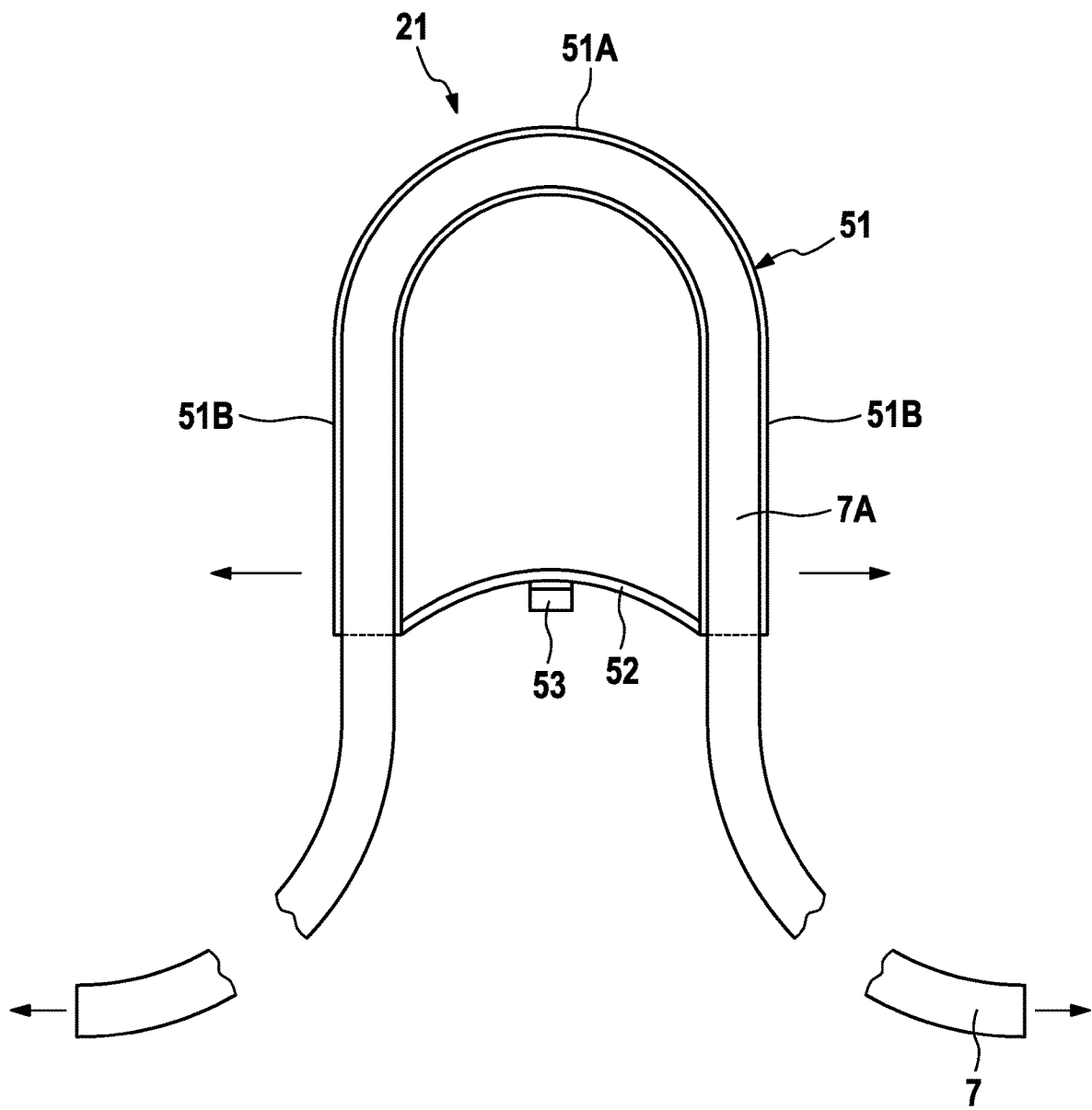
FIG. 10 shows a further embodiment of the device according to the invention for monitoring patient access.

FIG. 10 shows an embodiment in which the line guide 21 has an arc-shaped guide element 51, it being possible for the line segment 7A to be laid so as to fit therein. In the present embodiment, the arc-shaped guide element 51 is a curved, substantially U-shaped rail comprising a semi-circular portion 51A and two parallel straight-line portions 51B. The arc-shaped guide element 51 consists of a resilient material, for example plastics material, such that the guide element can bend. When tension is applied to the flexible line 7, the distance between the opposite outer ends of the guide element 51 increases, as indicated by arrows in FIG. 10. The guide element 51 may be a plastics material profile which encloses the line segment in part.

The apparatus 22 for situation detection has an elongate, strip-shaped element 52, one end of which is connected to one straight-line portion 51B and the other end of which is connected to the other straight-line portion 51B of the guide element 51, the strip-shaped element 52 preferably being fastened in the region of the ends of the guide element. The strip-shaped element 52, which may be a metal strip, is resiliently biased into a curved shape. If tension is applied to the flexible line 7, at least one of the two straight-line portions 51B of the guide element 51 is bent outwards, such that the strip-shaped element 52 is deformed counter to the bias and is no longer curved. When the strip-shaped element 52 is deformed, a switch 53 (merely shown schematically) is actuated. Instead of a switch, however, a strain gauge (not shown in FIG. 10) may also be provided on the strip-shaped element.

Figure 11:
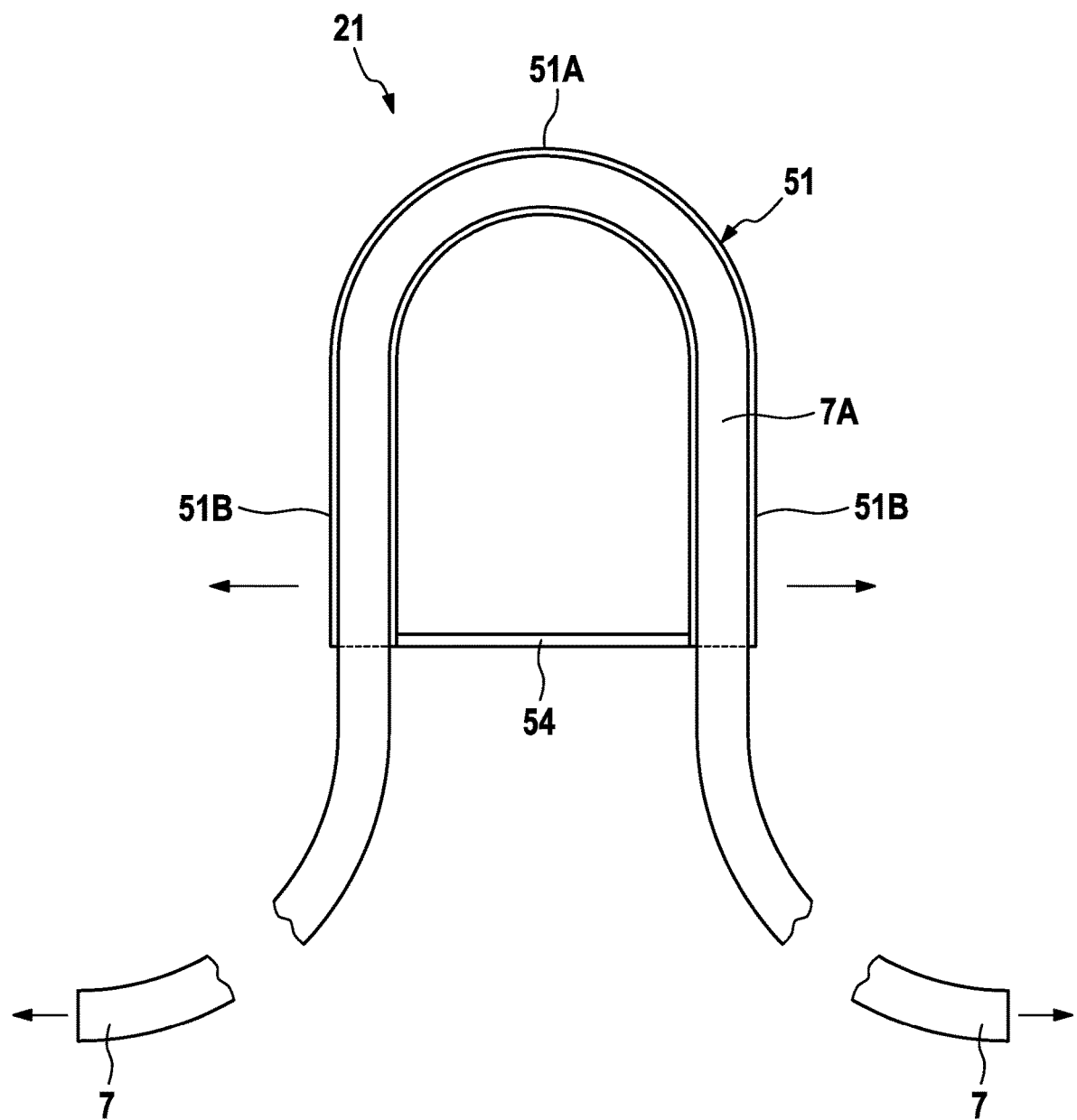
FIG. 11 shows an alternative embodiment of the device according to the invention from FIG. 10.

FIG. 11 shows an alternative embodiment, which differs from the embodiment from FIG. 10 in that the apparatus 22 for situation detection has an elongate element 54 made of an electrically conductive material, which is fastened to the ends of the straight-line portions 51B of the guide element 51. In the present embodiment, the elongate element 54 is an electrical wire, which is severed if at least one of the two straight-line portions 51B of the guide element 51 curves outwards when there is a change in situation of the line segment 7A due to applied tension. In an alternative embodiment, the apparatus 22 for situation detection has an evaluation unit 23, which is configured in such a way that the electrical resistance of the wire is monitored. When the resistance is zero, the control signal is generated.

Figure 12:
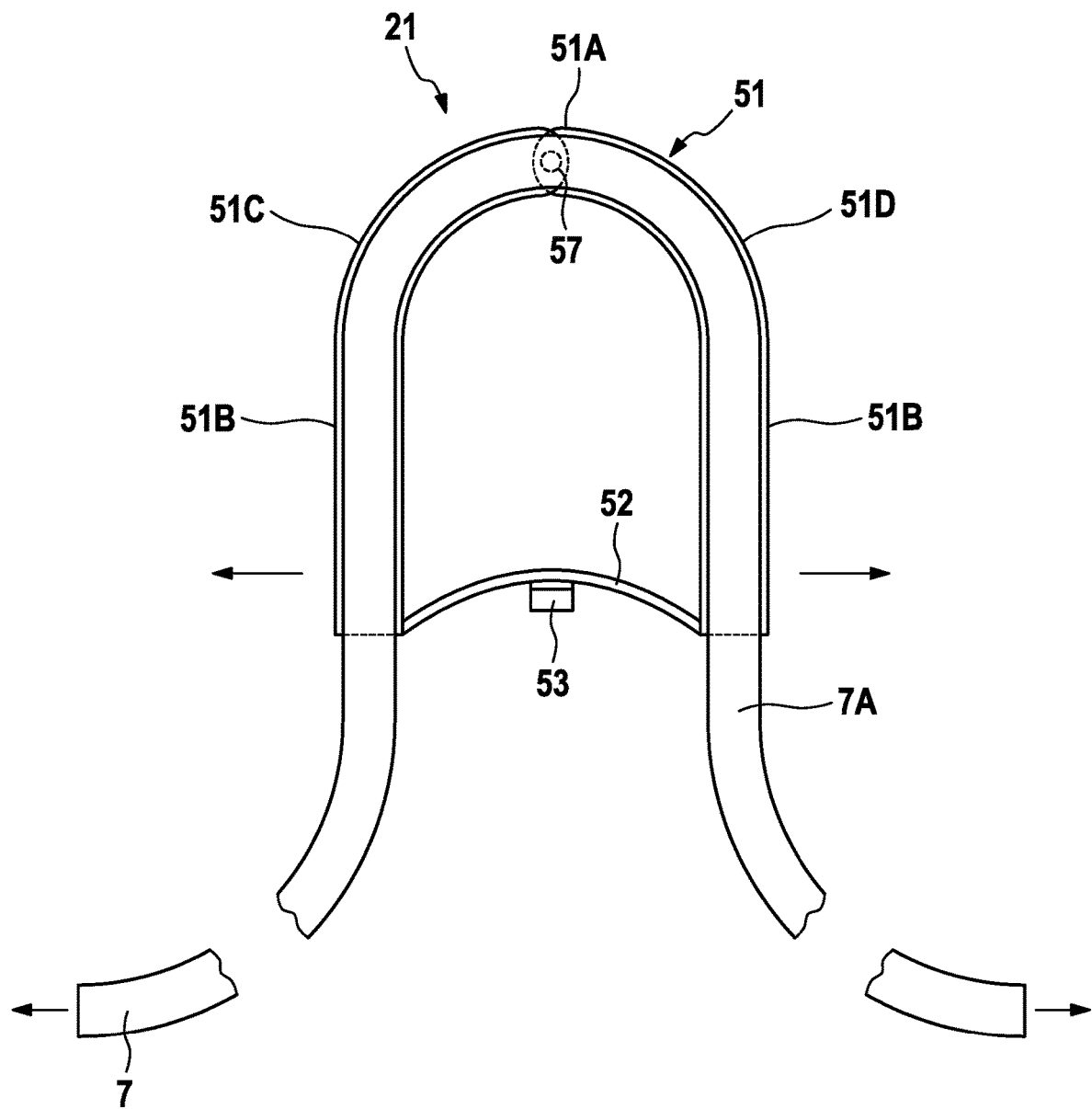
FIG. 12 shows a further embodiment of the device according to the invention for monitoring patient access.

FIG. 12 shows an alternative embodiment, which differs from the embodiment from FIG. 10 in that the guide element 51 has a first arc-shaped portion 51C for receiving a first sub-portion of the line segment 7A and a second arc-shaped portion 51D for receiving a second sub-portion of the line segment 7A. The mutually corresponding parts are again provided with like reference numerals. The first and second portions 51C, 51D of the guide element 51 are movably interconnected at the ends by means of an articulation 57, in such a way that the distance between the opposite free ends of the guide element increases when tension is applied to the flexible line, as again indicated by arrows. In this embodiment, the sub-portions may consist of a non-resilient material. Instead of a resilient strip-shaped element 52 as in FIG. 10, in particular a metal strip, in the embodiment in FIG. 12, a strain gauge or an electrical wire 54 (FIG. 11) may be provided for actuating a switch 53.

The invention claimed is:

1. A blood treatment device comprising an extracorporeal blood circuit comprising a flexible venous line having a venous puncture cannula, and a device for monitoring access to a patient for the blood treatment device, wherein
   the blood treatment device is configured such that blood is supplied to the patient via the flexible venous line,
   the flexible venous line comprises a plurality of spaced-apart markings, applied thereto,
   the device for monitoring access to the patient has (1) a line guide for guiding a line segment of the flexible venous line, (2) an apparatus for detecting a situation of the line segment guided by the line guide, and (3) an evaluation unit that is configured such that, when a change in the situation of the line segment due to tension applied to the flexible line, is detected, the evaluation unit concludes that incorrect vessel access is occurring,
   the apparatus for detecting the situation of the line segment guided by the line guide comprises a detection system configured to detect a change in situation of the plurality of spaced-apart markings and a change in a spatial position of the line segment relative to (a) the line guide, or (b) the apparatus for detecting the situation, or (c) both the line guide and the apparatus for detecting the situation, and
   the detection system is configured to measure a distance that the line segment moves relative to (a) the line guide, or (b) the apparatus for detecting the situation, or (c) both the line guide and the apparatus for detecting the situation, based on the change in situation of the plurality of spaced-apart markings.

2. The device according to claim 1, wherein the detection system comprises an optical image capture system and the optical image capture system is configured to detect the plurality of spaced-apart markings, applied to the flexible venous line, individually in succession.

3. The device according to claim 2, wherein
   the optical image capture system is configured to count when the markings are moved relative to the optical image capture system, as a result of the change in the situation of the flexible venous line and the markings passing through a detection region of the optical image capture system, and
   the evaluation unit is configured such that it compares a number of the markings counted by the optical image capture system with a predetermined threshold and concludes that there is the change in the situation of the flexible venous line due to the tension applied to the flexible venous line when the number of the markings counted is greater than the predetermined threshold.

4. The device according to claim 2, wherein
the optical image capture system is configured such that the plurality of spaced-apart markings provided on the flexible venous line is determined within an observation window,
the evaluation unit is configured such that the number of markings in the observation window is compared with a predetermined threshold, and
the evaluation unit concludes that there is the change in the situation of the flexible venous line due to the tension applied to the flexible venous line when the number of the markings in the observation window is less than the predetermined threshold.

5. The device according to claim 1, wherein the line guide is formed such that the line segment is guided in the shape of a loop that contracts when the tension is applied.

6. The device according to claim 5, wherein the line guide has a housing body comprising a first guide channel for receiving a first portion of the line segment of the flexible venous line, and a second guide channel for receiving a second portion of the line segment of the flexible venous line.

7. The device according to claim 6, wherein the guide channels are formed in first and/or second housing halves of the housing body.

8. The device according to claim 6, wherein the housing body comprises a first housing half and a second housing half and the first and/or second housing halves of the housing body are releasably or openably interconnected.

9. The device according to claim 1, wherein the apparatus for detecting the situation is configured such that a control signal is generated when the change in the situation of the line segment due to the tension applied to the flexible venous line, is detected.

10. A method for monitoring access to a patient for a device by means of which a liquid is withdrawn from a patient and/or supplied to the patient, in which blood of the patient is withdrawn from the patient via a flexible arterial line having an arterial puncture cannula and supplied to the patient via a flexible venous line having a venous puncture cannula, wherein
a line segment of the flexible venous line comprises a plurality of spaced-apart markings applied thereto and is guided by a line guide such that the line segment forms a loop or an arc,
a change in spatial position of the line segment forming the loop or arc, due to the tension applied to the flexible venous line, is monitored by a monitoring system,
the monitoring system comprises a detection system configured to detect a change in situation of the plurality of spaced-apart markings and a change in the spatial position of the line segment relative to (a) the line guide, or (b) the monitoring system, or (c) both the line guide and the monitoring system,
the detection system is configured to measure a distance that the line segment moves relative to (a) the line guide, or (b) the apparatus for detecting the situation, or (c) both the line guide and the apparatus for detecting the situation, based on the change in situation of the plurality of spaced-apart markings, and
the monitoring system concludes that incorrect vessel access is occurring if the spatial position of the line segment changes.

\* \* \* \* \*